United States Patent
Bzik et al.

(10) Patent No.: US 10,864,258 B2
(45) Date of Patent: *Dec. 15, 2020

(54) **METHOD FOR TREATING PANCREATIC CANCER WITH *TOXOPLASMA GONDII* VACCINE**

(71) Applicant: Trustees of Dartmouth College, Hanover, NH (US)

(72) Inventors: David J. Bzik, Grantham, NH (US); Barbara A. Fox, Grantham, NH (US); Kiah L. Sanders, West Lebanon, NH (US)

(73) Assignee: TRUSTEES OF DARTMOUTH COLLEGE, Hanover, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/787,488

(22) PCT Filed: Apr. 15, 2014

(86) PCT No.: PCT/US2014/034127
§ 371 (c)(1),
(2) Date: Oct. 28, 2015

(87) PCT Pub. No.: WO2014/179038
PCT Pub. Date: Nov. 6, 2014

(65) Prior Publication Data
US 2016/0067321 A1    Mar. 10, 2016

Related U.S. Application Data

(60) Provisional application No. 61/817,030, filed on Apr. 29, 2013.

(51) Int. Cl.
| | | |
|---|---|---|
| *A61K 39/00* | (2006.01) | |
| *A61K 39/39* | (2006.01) | |
| *A61K 39/002* | (2006.01) | |
| *C12N 9/88* | (2006.01) | |
| *C12N 9/10* | (2006.01) | |
| *C12N 9/00* | (2006.01) | |
| *C12N 9/86* | (2006.01) | |
| *C12N 9/02* | (2006.01) | |
| *C12N 1/36* | (2006.01) | |

(52) U.S. Cl.
CPC ........ *A61K 39/0011* (2013.01); *A61K 39/002* (2013.01); *A61K 39/39* (2013.01); *C12N 1/36* (2013.01); *C12N 9/001* (2013.01); *C12N 9/1018* (2013.01); *C12N 9/1077* (2013.01); *C12N 9/86* (2013.01); *C12N 9/88* (2013.01); *C12N 9/93* (2013.01); *A61K 2039/522* (2013.01); *A61K 2039/523* (2013.01); *A61K 2039/57* (2013.01); *A61K 2039/585* (2013.01); *A61K 2039/852* (2018.08)

(58) Field of Classification Search
None
See application file for complete search history.

(56) References Cited

U.S. PATENT DOCUMENTS

| 8,282,942 B2 | 10/2012 | Bzik et al. ................. 424/273.1 |
| 8,293,224 B2 | 10/2012 | Bzik et al. .................... 424/93.2 |
| 8,673,289 B2 | 3/2014 | Bzik et al. .................... 424/93.1 |
| 2010/0266491 A1 | 10/2010 | Farokhzad et al. .......... 424/1.29 |
| 2012/0045477 A1 | 2/2012 | Bzik et al. ................. 424/273.1 |
| 2012/0195961 A1 | 8/2012 | Kritikou et al. .............. 424/450 |

FOREIGN PATENT DOCUMENTS

| WO | PCT/US08/087081 | 7/2009 |
| WO | PCT/US12/060746 | 4/2013 |

OTHER PUBLICATIONS

Conejo-Garcia et al. "Vascular leukocytes contribute to tumor vascularization" Blood 2005 105:679-81.
Conejo-Garcia et al. "Ovarian carcinoma expresses the NKG2D ligand Letal and promotes the survival and expansion of CD28-antitumor T cells" Cancer Res. 2004 64:2175-82.
Conejo-Garcia et al. "Letal, A tumor-associated NKG2D immunoreceptor ligand, induces activation and expansion of effector immune cells" Cancer Biol. Ther. 2003 2:446-51.
Cubillos-Ruiz et al. "Polyethylenimine-based siRNA nanocomplexes reprogram tumor-associated dendritic cells via TLR5 to elicit therapeutic antitumor immunity" J. Clin. Invest. 2009 119:2231-44.
Cubillos-Ruiz et al. "Nanomolecular targeting of dendritic cells for ovarian cancer therapy" Future Oncol. 2009 5:1189-92.
Cubillos-Ruiz et al. "Blocking ovarian cancer progression by targeting tumor microenvironmental leukocytes" Cell Cycle 2010 9:260-8.
De Visser & Coussens "The inflammatory tumor microenvironment and its impact on cancer development" Contrib. Microbiol. 2006 13:118-37.
Dudley et al. "Adoptive transfer of cloned melanoma-reactive T lymphocytes for the treatment of patients with metastatic melanoma" J. Immunother. 2001 24:363-73.
Lollini et al. "Discovery of cancer vaccination protocols with a genetic algorithm driving an agent based simulator" Bmc Bioinformatics 2006 7:352.
Pan et al. "A recombinant Listeria monocytogenes vaccine expressing a model tumour antigen protects mice against lethal tumour cell challenge and causes regression of established tumours" Nat. Med. 1995 1:471-7.
Pan et al. "Regression of established tumors in mice mediated by the oral administration of a recombinant Listeria monocytogenes vaccine" Cancer Res. 1995 55:4776-9.
Pan et al. "Regression of established B16F10 melanoma with a recombinant Listeria monocytogenes vaccine" Cancer Res. 1999 59:5264-9.

(Continued)

*Primary Examiner* — Robert A Zeman
(74) *Attorney, Agent, or Firm* — Licata & Tyrrell P.C.

(57) ABSTRACT

Attenuated *Toxoplasma gondii* mutants and methods using the same as vaccines in the prevention or treatment pancreatic cancer are provided.

2 Claims, 2 Drawing Sheets

(56) References Cited

OTHER PUBLICATIONS

Paterson "Rational approaches to immune regulation" Immunol. Res. 2004 27:451-62.
Paterson & Ikonomidis "Recombinant Listeria monocytogenes cancer vaccines" Curr. Opin. Immunol. 1996 8:664-9.
Paterson & Maciag "Listeria-based vaccines for cancer treatment" Curr. Opin. Mol. Ther. 2005 7:464-60.
Rakoff-Nahoum & Medzhitov "Toll-like receptors and cancer" Nat. Rev. Cancer 2009 9:57-63.
Scarlett et al. "In situ stimulation of CD40 and Toll-like receptor 3 transforms ovarian cancer-infiltrating dendritic cells from immunosuppressive to immunostimulatory cells" Cancer Res. 2009 69:7329-37.
Sinnathamby, et al. "Priming and activation of human ovarian and breast cancer-specific CD8+ T cells by polyvalent Listeria monocytogenes-based vaccines" J. Immunother. 2009 32:856-69.
Steer et al. "Harnessing the immune response to treat cancer" 2010 Oncogene 29:6301-13.
Zitvogel & Kroemer "Anticancer immunochemotherapy using adjuvants with direct cytotoxic effects" J. Clin. Invest. 2009 119:2127-30.
Zou et al. "Immunosuppressive networks in the tumour environment and their therapeutic relevance" Nat. Rev. Cancer 2005 5:263-74.
ClinicalTrial.gov Identifier NCT01116245 dated Apr. 20, 2010.
ClinicalTrial.gov Identifier NCT00327652 dated May 17, 2006.
ClinicalTrial.gov Identifier NCT00585845 dated Dec. 22, 2007.
International Search Report and Written Opinion in PCT/US14/34127, dated Aug. 20, 2014, PCT.
International Preliminary Examination Report in PCT/US14/34127, dated Nov. 12, 2015, PCT.

METHOD FOR TREATING PANCREATIC CANCER WITH *TOXOPLASMA GONDII* VACCINE

This application is a U.S. National Stage Application of PCT/US2014/034127 filed Apr. 15, 2014 and claims the benefit of priority from U.S. Provisional Patent Application Ser. No. 61/817,030, filed Apr. 29, 2013, the contents of each of which are incorporated herein by reference in their entirety.

This application claims the benefit of priority from U.S. Provisional Patent Application Ser. No. 61/817,030, filed Apr. 29, 2013, the content of which is incorporated herein by reference in its entirety.

This invention was made with government support under contract number RO1 AI041930 awarded by the National Institutes of Health. The government has certain rights in the invention.

BACKGROUND

Pancreatic ductal adenocarcinoma (PDAC) is one of the most devastating cancers world-wide. Most cases present late and only 20% of PDAC patients live for longer than 6 months with any current therapy. Only 6% of patients survive longer than 5 years, and this survival rate has not changed in the last 40 years. PDAC patients do not respond effectively to either current chemotherapy or radiation therapy. Surgery, when it is possible, delays tumor progression, but the tumor essentially rapidly returns in an untreatable form.

It has been demonstrated that part of the function of the immune system is elimination of tumors (Steer, et al. (2010) *Oncogene* 29:6301-13; de Visser & Coussens (2006) *Contrib. Microbiol.* 13:118-37; Lollini, et al. (2006) *BMC Bioinformatics* 7:352). Almost without exception, any tumor that manifests clinically has evaded immune surveillance by developing multiple immunosuppression mechanisms, such as expressing immunosuppressive mediators or calling in immunosuppressive cells with chemoattractants (Zou, et al. (2005) *Nat. Rev. Cancer* 5:263-74; Cubillos-Ruiz, et al (2009) *J. Clin. Invest.* 119:2231-44; Cubillos-Ruiz, et al. (2009) *Future Oncol.* 5:1189-92; Cubillos-Ruiz, et al. (2010) *Cell Cycle* 9:260-8; Scarlett, et al. (2009) *Cancer Re.* 69:7329-37; de Visser & Coussens (2006) supra; Conejo-Garcia, et al. (2004) *Cancer Res.* 64:2175-82; Conejo-Garcia, et al. (2003) *Cancer Biol. Ther.* 2:446-51; Conejo-Garcia, et al. (2005) *Blood* 105:679-81). Supporting ongoing anti-tumor immune responses offers great promise to complement treatments targeting the tumor cell cycle or cellular signaling pathways, and already represent the most effective intervention against otherwise incurable melanomas (Dudley, et al. (2001) *J. Immunother.* 24:363-73; Rosenberg & Dudley (2004) *Proc. Natl. Acad. Sci. USA* 101: 14639-45; Zitvogel & Kroemer (2009) *J. Clin. Invest.* 119: 2127-30). However, it has become increasingly clear that effective strategies to break tumor-mediated immunosuppression will be required to elicit comparable protective anti-tumor immunity against the most lethal cancers. This is because effective antitumor T cell responses mediated by CD4 and CD8 T-cells are not effectively activated in immune-suppressed tumor environments unless the immunosuppression can be reversed.

The immune system has evolved to recognize and respond to microorganisms and therefore, microorganisms or their constituents are powerful adjuvants (Rakoff-Nahoum & Medzhitov (2009) *Nat. Rev. Cancer* 9:57-63). Each microorganism has unique characteristics in how they interact with the immune system and therefore each microorganism has unique adjuvant characteristics. Recently, the rapidly developing understanding about the interaction of innate and adaptive immunity and the associated understanding of how adjuvants work has fostered renewed interest in using microorganisms as adjuvants to stimulate antitumor immune responses (Paterson & Maciag (2005) *Curr. Opin. Mol. Ther.* 7:464-60; Paterson (2004) *Immunol. Res.* 27:451-62; Paterson & Ikonomidis (1996) *Curr. Opin. Immunol.* 8:664-9; Pan, et al. (1995) *Nat. Med.* 1:471-7; Pan, et al. (1995) *Cancer Res.* 55:4776-9; Pan, et al. (1999) *Cancer Res.* 59:5264-9; Sinnathamby, et al. (2009) *J. Immunother.* 32:856-69). This approach is strengthened by the ability to genetically manipulate the microorganisms to make them safer and more effective (Paterson & Ikonomidis (1996) supra). The focus of these studies has been on using *Listeria monocytogenes*, a gram positive bacterium that can live either within or outside of cells (Paterson & Maciag (2005) supra; Paterson (2004) supra; Paterson & Ikonomidis (1996) supra; Pan, et al. (1999) supra; Pan, et al. (1995) supra; Sinnathamby, et al. (2009) supra). Attenuated *Listeria* has been used in multiple phase I and II clinical trials against cervical, and prostate cancers (ClinicalTrial.gov Identifier NCT01116245, NCT00327652, NCT00585845, NCT0080007).

SUMMARY OF THE INVENTION

The present invention features a method for preventing or treating pancreatic cancer by administering to a subject in need of treatment an effective amount of an attenuated mutant of *Toxoplasma gondii*. In some embodiments, the attenuated mutant includes a knockout mutation of one or more genes of the de novo pyrimidine synthesis pathway and/or pyrimidine salvage pathway, e.g., a gene encoding carbamoyl phosphate synthetase II, aspartate transcarbamylase, dihydroorotase, dihydroorotase dehydrogenase, orotate phosphoribosyltransferase, or orotidine 5'-monophosphate decarboxylase, uridine phosphorylase, purine nucleoside phosphorylase, or uracil phosphoribosyltransferase). In another embodiment, the *T. gondii* is attenuated by γ-irradiation. In still other embodiments, the attenuated mutant expresses one or more tumor antigens or exogenous proteins. In yet other embodiments, the attenuated mutant is administered intravenously, intratumorally, intraperitoneally, or via irradiated whole cell tumor vaccine.

DETAILED DESCRIPTION OF THE INVENTION

Figure 1A:
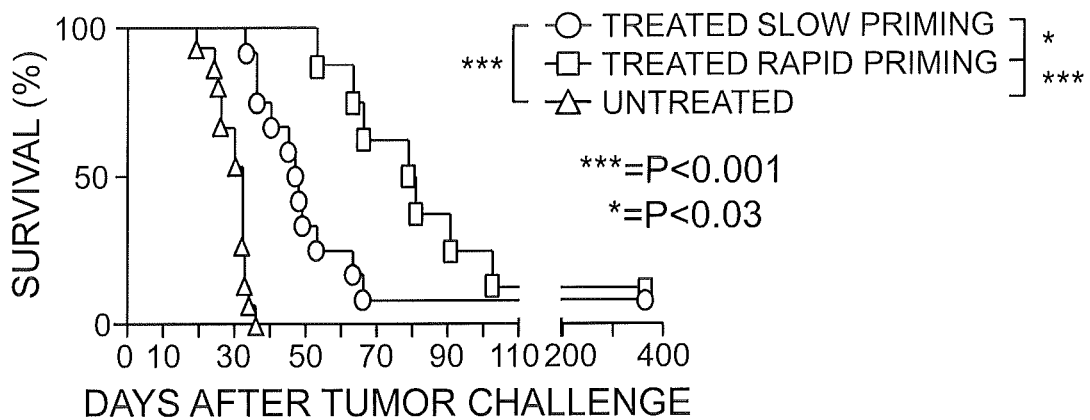
FIGS. 1A and 1B shows that CPS and OMUP mutant treatment confers a cure rate and significant advantage in a dose-dependent manner. Pan02 ($1\times10^6$) cells were injected intraperitoneally into each mouse (n=8) on day 0. One week after injection of Pan02 cells, mice were treated with CPS (FIG. 1A) or OMUP (FIG. 1B) mutant on a slow dose or rapid dose treatment schedule. Slow priming-treated mice were injected with the CPS or OMUP mutant on days 7, 19 and 31 post-tumor inoculation. Rapid priming-treated mice were injected with CPS or OMUP mutant on days 7, 8, 11, 12, 24 and 36 post-tumor inoculation.
Figure 1B:
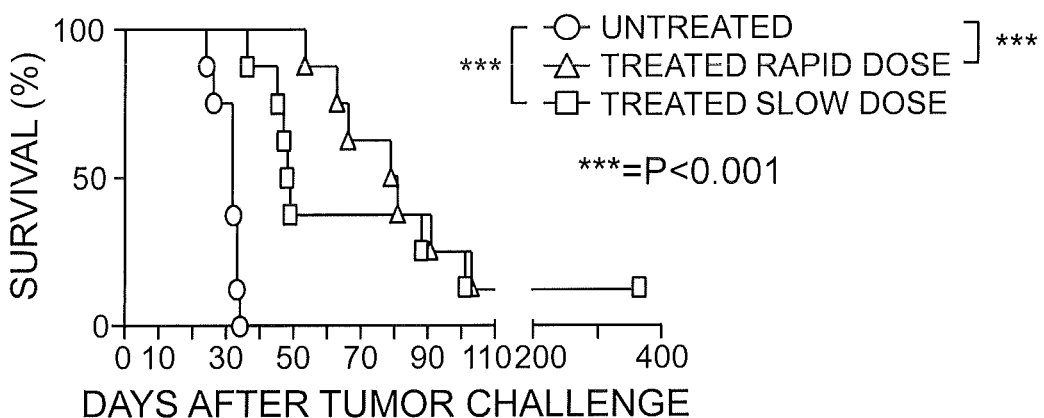

*Toxoplasma gondii*, an obligate intracellular apicomplexan parasite of mammals, has been shown to inhibit angiogenesis (Hunter, et al. (2001) *J. Immunol.* 166:5878-81; Kim, et al. (2007) *J. Korean Med. Sci.* 22:S38-46); *T. gondii* antigens have been shown to decrease fibrosarcoma growth (Darani, et al. (2009) *Korean J. Parasitol.* 47:175-7), enhance dendritic cell-based cancer vaccines (Motamedi, et al. (2009) *Clin. Vaccine Immunol.* 16:1393-8); and formalin-fixed *T. gondii* has been shown to exhibit antitumor activity (Suzuki, et al. (1986) *J. Biol. Response Mod.* 5:288-293). Using attenuated mutant strains of *T. gondii* (i.e., CPS and OMUP mutants) that are non-reverting and cannot replicate in vivo, it has now been found that *T. gondii* serves as an antitumor adjuvant in pancreatic cancer (FIGS. 1A and 1B). It was observed that treatment with the *T. gondii* mutants conferred a measureable cure rate in mice bearing disseminated late-stage pancreatic cancer (Pan02 or Panc02 mouse model) as well as a uniformly high survival advantage in this established mouse model of pancreatic cancer (Corbett, et al. (1984) *Cancer Res.* 44:717-26). Moreover, survival advantages increased with additional *T. gondii* mutant treatments, wherein mice receiving six treatments survived longer (e.g., >1 year) than mice receiving three treatments. The antitumor effect of the CPS mutant in pancreatic cancer relies on a living parasite (FIG. 2), as well as the production of IL-12 and IFN-gamma, an intact MyD88 signaling pathway and CD8 T cells. However, the antitumor effect was not dependent upon CD4 T cells or NK cells. In addition, it was observed that the attenuated *T. gondii* stimulates a pancreatic tumor-specific CD8 T cell response, which indicates that this vaccine treatment spontaneously elicits specific CD8 T cell vaccine responses that target the tumor. Moreover, uracil auxotroph invasion of tumor cells acts as a powerful adjuvant that markedly increases vaccine efficacy for the prevention (FIGS. 3A and 3B) and treatment (FIG. 4) of cancer. The elicitation of these anti-tumor responses highlights the use of attenuated, non-replicating *T. gondii* mutants as an immunotherapeutic agent.

Accordingly, the present invention provides a method for the prevention and treatment of pancreatic cancer using a vaccine containing an attenuated mutant of *T. gondii*. As is conventional in the art, the term "attenuated" refers to a weakened and/or less vigorous strain of *T. gondii*, which preferably does not revert to wild-type (i.e., non-reverting) and cannot replicate in vivo. Desirably, the attenuated mutant of the invention is capable of stimulating an immune response and creating immunity but not causing illness. Attenuation can be achieved by conventional methods including, but not limited to, γ-irradiation or the generation of a pyrimidine auxotroph. A pyrimidine auxotroph of the invention can be produced by disrupting mechanisms for pyrimidine acquisition including, mutating proteins involved in pyrimidine synthesis along with those of pyrimidine salvage (e.g., enzymes or transporters). Specifically, pyrimidine auxotrophs can be produced by knocking out or mutating one or more of CPSII (carbamoyl phosphate synthetase II; Gene loci ID 583.m05492), OMPDC (orotidine 5'-monophosphate decarboxylase; Gene loci ID 55.m04842), OPRT (orotate phosphoribosyltransferase; Gene loci ID 55.m04838), DHO (dihydroorotase; Gene loci ID 83.m00001), aspartate transcarbamylase (ATC), dihydroorotase dehydrogenase (DHOD), uridine phosphorylase (UP), uracil phosphoribosyltransferase, purine nucleoside phosphorylase (e.g., PNP), and/or a nucleobase/nucleoside transporter of pyrimidine bases or nucleosides (e.g., NT2 or NT3). Indeed, any single knockout or combination of knockouts is contemplated to achieve an attenuated strain. By way of illustration, this invention embraces an attenuated strain or vaccine strain constructed by a single knockout in any of the six de novo pyrimidine biosynthetic genes (CPS, ATC, DHO, DHOD, OPRT or OMPDC), knockout of two or more genes of the de novo pyrimidine synthetic pathway, or knockout of a de novo pyrimidine synthesis gene in combination with a knockout in a pyrimidine salvage gene (e.g., coding for enzymes UP, PNP, or uracil phosphoribosyltransferase) and/or in combination with a knockout of a nucleobase/nucleoside transporter of pyrimidine bases or nucleosides. Such attenuated mutants can be generated by substitution, deletion or insertion as is conventional in the art. It is contemplated that because an attenuated auxotroph of *T. gondii* (e.g., a CPSII or OMUP knockout) induces a Th-1 immune response, any attenuated mutant of *T. gondii* can be used as a vaccine without the complication of dead host cells and infectious dissemination of *T. gondii* in the host. Thus, particular embodiments of the present invention embrace a vaccine including an attenuated pyrimidine auxotroph of *T. gondii*. See U.S. Pat. Nos. 8,282,942, 8,293,224 and 7,803,389, incorporated herein by reference in their entireties.

In addition to attenuation, mutants of the invention can be multiply crippled strains of *T. gondii* that exhibit other desirable defects such as loss of ability to develop into tissue cysts, loss of sexual stages, loss of oocyst formation, or other developmental or phenotypic defects or changes that would enhance the efficacy or safety of vaccines based on mutants of the invention. For example, while certain proteins have been shown to contain T-cell epitopes (e.g., GRA4, GRA6, and ROP7) and may be important in immunity, other proteins signal to host cells (e.g., ROP16, ROP18) and may present tools to manipulate mammalian cells. See Mercier, et al. (1998) *Infect. Immun.* 66:4176-4182; Lecordier, et al. (1999) *Mol. Biol. Cell.* 10(4):1277-87; Igarashi, et al. (2008) *Gen. Mol. Res.* 7(2):305-313. Therefore, certain embodiments of this invention embrace mutating or deleting any secreted protein of the parasite, for example one or more of the GRA genes (i.e., GRA2, GRA3, GRA4, GRA5, GRA6, GRA7, GRA8, and GRA9) and/or ROP genes (i.e., ROP16 and ROP18) to modify or improve the ability of attenuated *Toxoplasma* to present antigens in vaccine formulations. Such an approach could improve vaccine efficacy and provide insight into how to manipulate host cells for new therapeutics. The GRAs occupy the vacuole space or vacuole membrane, which are key intersections that exogenous antigens (i.e. a vaccine formulation expressed by attenuated *T. gondii*) must pass through to get presented onto the MHCI or MHCII of the host cell.

As is conventional in the art, a gene or locus is the coding region and expression control sequences (e.g., promoter, enhancer, and the like) of a protein. In the context of the present invention, a mutation includes a substitution, deletion, or insertion at the desired locus which decreases or abolishes the activity of the protein encoded by said locus. For example, amino acid substitutions or insertions at the enzyme active site are expected to significantly decrease or abolish activity. Similarly, amino acid substitutions or insertions which destabilize (e.g., enhance degradation) the desired mRNA or protein can be used to decrease or abolish the activity a protein, e.g., CPSII. Moreover, promoter mutations which decrease or abolish expression of a protein can be used to decrease or abolish activity. In particular embodiments, a mutant of the present invention lacks all or a substantial portion (e.g., more than 50, 60, 70, 80 or 90%) of the nucleic acids encoding a protein of interest. As is conventional in the art, the nucleic acids encoding a protein of interest include the nucleic acids beginning at the initiation codon (i.e., ATG) and ending at the termination codon (e.g., TGA, TAA and TAG). In some embodiments, a mutant of the present invention lacks all, or a substantial portion, of the nucleic acids encoding CPSII or OMPDC. Thus, in one embodiment, the attenuated mutant *T. gondii* of the invention is an attenuated CPSII or OMPDC knock out mutant.

A mutant of the present invention can be generated using any suitable method conventionally employed for producing gene knockout mutants of *T. gondii*. For example, the mutant can be obtained by the single cross-over integration, e.g., as disclosed by Fox & Bzik ((2002) *Nature* 415(6874):926-9) or using a double-crossover gene replacement, e.g., as disclosed by Mercier, et al. ((1998) *Infect. Immun.* 66:4176-82). See also Wang, et al. (2002) *Mol. Biochem. Parasitol.* 123(1):1-10, or by using KU80 mutant strains for precise gene replacement as described in U.S. Pat. No. 7,803,389, incorporated herein by reference. In general, the generation of a mutant *T. gondii* includes isolating the nucleic acid molecule of interest from *T. gondii*; replacing, mutating, substituting or deleting all or a portion (e.g., one or more bp) of the gene to disrupt the promoter, regulatory sequence(s) and/or coding region of the protein; and integrating the disrupted molecule (e.g., via single- or double-crossover homologous recombination events) into the genome of *T. gondii*. Upon selection, i.e., marker protein expression or genomic DNA analysis, a knockout mutant is obtained. In particular embodiments, the selectable marker is selected for by positive and negative selection (e.g., HXGPRT), such that the selectable marker can be easily deleted from the targeted locus by homologous recombination and, upon negative selection, recovered for use again in a sequential process of positive and negative selection to create strains harboring multiple gene knockouts or replacements. Disruption of all or a portion of a gene of interest can be achieved by, e.g., replacing the coding sequence with a nucleic acid molecule encoding selectable marker, replacing the coding sequence with a nucleic acid molecule encoding an exogenous protein, substituting the promoter with a mutated promoter which can no longer be recognized by *T. gondii* transcription proteins (i.e., a promoter mutation), etc. As is known to the skilled artisan, subsequent restriction endonuclease digestion and Southern blot analysis of the mutant *T. gondii* genomic DNA can be used to confirm the knockout.

As will be appreciated by the skilled artisan, any suitable marker-encoding nucleic acid can be used to identify a *T. gondii* which has been transformed so long as it can be phenotypically detected in the mutant strain. Suitable marker proteins include, but are not limited to, positive and negative selectable markers such as HXGPRT, thymidine kinase, hygromycin resistance, cytosine deaminase, DHFR (dihydrofolate reductase), bleomycin, chloramphenicol acetyl transferase, or combinations thereof. It is contemplated that the nucleic acid molecule encoding the marker protein can be used to replace or substitute all or a portion of the promoter or coding sequence of the locus of interest to generate a knockout or mutant.

In an alternative embodiment, the attenuated mutant *T. gondii* of the invention is a γ-irradiated attenuated mutant strain of *T. gondii*. The use of γ irradiation to attenuate *T. gondii* is described in the art (Dubey, et al. (1998) *Int. J. Parasitol.* 28:369-75; Kook, et al. (1995) *Korean J. Parasitol.* 33:173-8). Specifically, $^{137}$Cs irradiation of sporulated oocysts has been shown to yield infective sporozoites, which are capable of penetrating enterocytes and all cells in the lamina propria, but not capable of inducing a viable infection. In particular, when attenuated by γ irradiation, it is desirable that the attenuated mutant maintains the ability to invade cells, including DC and myeloid cells, to provide optimal antitumor responses. In this respect, it has been demonstrated that a killed CPS mutant (non-invasive) does not provide the tumor survival benefit. Given that invasion injects specialized parasite effector molecules into the host cell cytoplasm thereby seizing control of the host cell (Butcher, et al. (2011) *PLoS Pathogens* 7(9):e1002236; Fentress, et al. (2010) *Cell Host Microbe* 8(6):484-95; Jensen, et al. (2011) *Cell Host Microbe* 9(6):472-83; Saeij, et al. (2006) *Science* 314(5806):1780-3; Taylor, et al. (2006) *Science* 314(5806):1776-80; Saeij, et al. (2007) *Nature* 445(7125):324-7; Peixoto, et al. (2010) *Cell Host Microbe* 8(2):208-18), invasion is a key component to the effectiveness of using *T. gondii* in a vaccine.

Mutants of this invention can be produced from a virulent type I strain such as RH (as exemplified herein), or a type II strain as well as a type III strain so that the underlying development of tissue cysts as well as oocysts in *Toxoplasma* infection can be analyzed.

While the mutant *T. gondii* of this invention may be used as is in the prevention or treatment of cancer, the mutant can also be further modified to deliver one or more tumor antigens. Specific examples of tumor antigens include, but are not limited to, annexinA2 (US 2011/0293608), plectin-1 (WO 2009/129220), fetoacinar pancreatic protein (WO 2005/095594) tubulin tyrosine ligase-like family member (TTLL4; WO 2010/023856) and the tumor differentiation antigen mesothelin (WO 1997/025068). In one embodiment, the tumor antigen is expressed by *T. gondii*. In another embodiment, the tumor antigen is expressed by *T. gondii*, secreted into the parasite vacuole and eventually into the cytosol of the mammalian host cell. The *T. gondii*-expressed tumor antigen subsequently enters the mammalian antigen presenting cell's (APC) antigen processing and presenting pathway as a substrate for generation of class I and class II peptides which generate CD8 and CD4 T cell responses. Accordingly, in one embodiment of the present invention, an attenuated mutant of the invention harbors nucleic acid molecules encoding one or more tumor antigens.

It is further contemplated that an attenuated mutant of *T. gondii* can be used to express any exogenous protein one would want to express within a mammalian host cell. This could include therapeutic peptides or proteins, e.g., therapeutic antibodies, e.g., r84 (Sullivan, et al. (2010) *PLoS ONE* 5(8): e12031), proteins (e.g., interferons, blood factors, erythropoietin, and blood clotting factors), or enzymes (e.g., asparaginase, catalase, lipase, and tissue plasminogen activator) used in the treatment of diseases or conditions. Such proteins are routinely expressed in other systems, e.g., yeast, mammalian cells lines, bacteria or insect cells, such that one skilled in the art could readily obtain nucleic acids encoding such proteins and express them in a mutant *T. gondii*.

The *T. gondii* mutant of the present invention can accommodate multiple expression constructs. Therefore, nucleic acid molecules encoding exogenous proteins, antigens and the like can be integrated into the *T. gondii* genome, e.g., as part of the nucleic acid molecule used to disrupt the promoter, regulatory sequences, or open reading frame of a protein of the pyrimidine synthesis pathway or at any other suitable location in the genome (e.g., at non-essential locus).

The basic criteria for exogenous protein and tumor antigen expression are that the gene is a non-*T. gondii* gene or coding sequence and the gene or coding sequence is able to be expressed directly or indirectly from a recombinant molecule in a *T. gondii* cell. In this regard, it is desirable that the promoter employed is recognizable by *T. gondii*. Moreover, it is desirable that the promoter promotes transcription of the protein coding sequence when the *T. gondii* is inside mammalian cells. To this end, particular embodiments embrace the use of a *T. gondii* promoter. Known promoter and other regulatory elements (e.g., 5' UTR, 3' UTR, etc.) which can be operably linked to the coding sequence of an exogenous protein of interest so that the exogenous protein is expressed in *T. gondii* include, but are not limited to, sequences from the *T. gondii* SAG1 gene (Striepen, et al. (1998) *Mol. Biochem. Parasitol.* 92(2):325-38) or the *T. gondii* NTPase gene (Robibaro, et al. (2002) *Cellular Microbiol.* 4:139; Nakaar, et al. (1998) *Mol. Biochem. Parasitol.* 92(2):229-39). Alternatively, suitable regulatory sequences can be obtained by known trapping techniques. See, e.g., Roos, et al. (1997) *Methods* 13(2):112-22. Promoters of use in accordance with the present invention can also be stage-specific promoters, which selectively express the exogenous protein(s) or antigen(s) of interest at different points in the obligate intracellular *T. gondii* life cycle. Moreover, it is contemplated that an endogenous promoter can be used to drive expression of the exogenous protein or antigen by, e.g., site-specific integration at the 3' end of a known promoter in the *T. gondii* genome.

When employed as a vaccine for generating an immune response and providing prevention or treatment of pancreatic cancer, particular embodiments provide that the mutant *T. gondii* is in admixture with a pharmaceutically acceptable carrier. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000. Furthermore, it has now been shown that ex vivo loading of dendritic cells, macrophages, and peritoneal cells with a CPS mutant, then immunizing an animal with these loaded cells leads to successful immunization. For example, dendritic cells loaded with a CPS mutant provides the strongest immune response in animals and produces long lasting CD8 T cell responses and long lasting immune memory. Accordingly, it is contemplated that a *T. gondii* mutant of the invention which is also a pyrimidine auxotroph can be administered via loading of dendritic cells, macrophages, and/or peritoneal cells.

Further, as demonstrated herein, an attenuated *T. gondii* mutant, in particular a mutant that expresses a tumor antigen, provides a potent adjuvant effect when used in combination with an irradiated tumor vaccine. Therefore, in one embodiment, the attenuated *T. gondii* mutant is administered via an irradiated whole cell tumor vaccine.

Administration of a mutant *T. gondii* disclosed herein can be carried out by any suitable means, including intraperitoneal, subcutaneous, intravenous or intramuscular injection, intratumoral, orally, intra-spinal, intra-cranial, intra-organ (for example pancreas), or by topical application (typically carried in a pharmaceutical formulation) to an airway surface. Topical application to an airway surface can be carried out by intranasal administration (e.g., by use of dropper, swab, or inhaler which deposits a pharmaceutical formulation intranasally). Oral administration can be in the form of an ingestible liquid or solid formulation. In particular embodiments, a *T. gondii* mutant is formulated for administration via intraperitoneal, intratumoral, intranasal or intravenous routes.

An attenuated mutant *T. gondii* or vaccine containing the same can be employed in various methods inducing an immune response and preventing or treating pancreatic cancer. Such methods generally involve administering to a subject in need of treatment an effective amount of an attenuated mutant *T. gondii* or vaccine of the present invention thereby generating an immune response and preventing or treating the subject's pancreatic cancer. Pancreatic cancers that can be prevented or treated with the instant attenuated mutant *T. gondii* or vaccine include, but are not limited to, pancreatic cancers such as pancreatic endocrine tumors (PET), e.g., gastrinoma, insulinoma, somatostatinoma, VIPoma, or glucagonoma; pancreatic exocrine cancers such as pancreatic cancer ductal adenocarcinoma (PDAC), adenosquamous carcinomas, signet ring cell carcinomas, hepatoid carcinomas, colloid carcinomas, undifferentiated carcinomas, and undifferentiated carcinomas with osteoclast-like giant cells; and pancreatic cystic neoplasms. In particular embodiments, the pancreatic cancer is PDAC.

An effective amount, as used in the context of the instant invention, is an amount which produces a detectable immune response (e.g., a Th-1 response, natural granulocyte, neutrophil, macrophage, GR1+ macrophage, B cell, or T cell immune response) or antibody production and reduces or prevents the signs or symptoms of pancreatic cancer. In accordance with some embodiments, the *T. gondii* mutant expresses an exogenous antigen thereby generating protective immunity against the pancreatic cancer from which the antigen was derived or associated. However, in other embodiments, the *T. gondii* mutant of the invention alone is sufficient to generate an immune response thereby treating or having effect on the severity of the pancreatic cancer. Thus, an effective amount of a *T. gondii* mutant of the invention prevents or treats the signs or symptoms of pancreatic cancer, or diminishes pancreatic cancer progression or spread (e.g. metastasis). Responses to administration can be measured by analysis of subject's vital signs, monitoring T cell responses, monitoring production of IFN-γ, IL-12p40, and/or IL-12p70, or monitoring chemokines CCL5 or CXCL1 according to the methods disclosed herein or any suitable method known in the art.

While the compositions and methods of this invention find application in the prevention and treatment of pancreatic cancer in mammals, in particular humans, the invention should be construed to include administration to a variety of animals, including, but not limited to, cats, dogs, horses, cows, cattle, sheep, goats, birds such as chickens, ducks, and geese. Subjects benefiting from prophylactic or therapeutic treatment with the attenuated mutant *T. gondii* include subjects with a positive diagnosis of early or late stage pancreatic cancer, subjects at risk of developing pancreatic cancer (e.g., because of family history or exposure to a carcinogen), and subjects who have had successful treatment of a primary tumor and are at risk of developing or have developed a secondary or metastatic tumor.

The precise schedule for administration can be determined by a skilled practitioner. Administration can be given initially in a single dose schedule, or by rapid priming of multiple repeated doses spaced 6 to 24 hours apart. This initial treatment can be followed by a multiple dose schedule in which a primary course of treatment can be with 1-10 separate doses, followed by other doses given at subsequent time intervals required to maintain and or reinforce the response, for example, at 12 days to 4 months for a second dose, and if needed, subsequent dose(s) after several weeks or months.

The exact dosage for administration can be determined by the skilled practitioner, in light of factors related to the subject that requires prevention or treatment. Dosage and administration are adjusted to provide sufficient levels of the composition or to maintain the desired effect of preventing or reducing signs or symptoms of pancreatic cancer, or reducing severity of the disease. Factors which may be taken into account include the severity of the disease state, general health of the subject, age, weight, and gender of the subject, diet, time and frequency of administration, drug combination(s), reaction sensitivities, and tolerance/response to therapy.

The following non-limiting examples are provided to further illustrate the present invention.

Example 1

Materials and Methods

Parasites.

*Toxoplasma gondii* RH strain or attenuated uracil auxotroph mutants OMUP (Δku80ΔompdcΔup::HXGPRT) or cpsI (CPS mutant) have been described (Fox & Bzik (2002) Nature 415(6874):926-9; Fox & Bzik (2010) Infect. Immun. 78:3744-52) and were cultured according to known methods (Fox & Bzik (2002) supra). In some experiments, tachyzoites were further inactivated by γ-irradiation (15 krad).

Mice.

6-8 week old C57BL/6, IL-12p35$^{-/-}$, IFN-γ$^{-/-}$, MyD88$^{-/-}$, and CD8a$^{-/-}$ were purchased from Jackson Laboratory.

Cell Lines.

The murine pancreatic adenocarcinoma (Pan02) cell line was acquired from the Division of Cancer Treatment Tumor Repository (National Cancer Institute). Pan02 cells were maintained in high glucose RPMI supplemented with 10% fetal bovine serum (FBS) and penicillin/streptomycin. ID8-GFP cells were maintained in high glucose DMEM supplemented with 10% FBS and penicillin/streptomycin. Human foreskin fibroblasts (HFF) cultures were maintained in EMEM supplemented with 10% FBS and penicillin/streptomycin.

Parasites.

Tachyzoites of *T. gondii* were grown in HFF and supplemented with uracil to allow for replication (Fox & Bzik (2002) Nature 415:926-929). To harvest parasites for injection, tachyzoites were purified through a 3.0 µm nucleopore membrane and washed with phosphate-buffered saline (PBS).

Inoculation and Treatment of Pancreatic Tumors. For survival experiments and ELISAs, $1.0 \times 10^6$ Pan02 cells were injected i.p. and tumor was established for 7 days. In cellular analysis and ELISPOT, $1.0 \times 10^6$ Pan02 cells were injected i.p. and established for 14 days. For "slow dose," mice were treated i.p. at day 7, 19 and 31, "rapid dose" mice were treated i.p. at day 7, 8, 11, 12, 24 and 36. For ELISAs, animals were treated once at day 7. For ELISPOT, mice were treated once at day 14.

Flow Cytometry for Cellular Analysis.

Animals were treated 14 days post-tumor inoculation. For flow analysis, on the indicated day post-treatment/tumor inoculation, total PECs were isolated. For intracellular stains, cells were incubated with Brefeldin A for 5 hours at 37° C. Depletion of erythrocytes was carried out using red blood cell lysis buffer (eBioscience). Cells were then counted and stained. AF647-conjugated anti-mouse CD45, PE-conjugated and AF647-conjugated anti-mouse CD11b, Brilliant Violet 421-conjugated anti-mouse CD11c, PE-Cy7-conjugated anti-mouse CD4 and PE-conjugated anti-mouse CD4, AF647-conjugated anti-mouse CD19, PE-Cy7-conjugated anti-mouse F4/80, Brilliant Violet 421-conjugated anti-mouse CD3, PE-Cy7-conjugated anti-mouse Gr-1, PE-conjugated and AF647-conjugated anti-mouse CD8b, AF488-conjugated anti-mouse/human CD44, PE-Cy7-conjugated anti-mouse CD62L, AF647-conjugated anti-mouse CD69, PE-conjugated anti-mouse IFN-γ, PE-conjugated anti-mouse IL-12/IL-23p40, PE-conjugated anti-mouse CD86, PE-conjugated anti-mouse CD80 and CD16/32 blocking antibody were purchased from Biolegend.

Depleting Antibodies.

Anti-CD4, anti-CD8, and isotype control (rat IgG2a) were purchased from BioXCell and administered at doses of 500 µg on day −1 and 250 µg on days 0 and 3 post-treatment. Greater than 99% depletion of target T cell populations was observed using flow cytometry. Anti-NK1.1 was administered at doses of 50 µg on days −2, 0, and post-treatment. Greater than 99% depletion of target NK cell populations was observed using flow cytometry.

Cytokine Measurements.

Serum from treated or untreated mice was collected at days 1, 2, 4, 6 and 7. Whole blood was incubated at room temperature for 1 hour to clot and centrifuged for 10 minutes at 1500 rcf at 4° C. Peritoneal fluid was collected and centrifuged at 1200 rpm at 4° C. Following centrifugation, the supernatant was collected. Both blood serum and peritoneal supernatant were frozen at −80° C. until needed. IFN-γ, IL-12p40, and IL-12p70 in serum and supernatants were determined using OPTEIA ELISA kits and reagent sets (BD Biosciences).

IFN-γ ELISPOT.

CD8$^+$ T cells were isolated from spleens and purified using EASYSEP Mouse CD8$^+$ T cell Enrichment Kit (Stem Cell Technologies). Cells were plated at a 10:1 ratio of T cells and irradiated target Pan02 cells, HFF cells, or ID8-GFP cells in the presence of $5.0 \times 10^4$ irradiated splenocytes.

Statistics.

Statistical analysis was performed using Graphpad Prism 5 software. P-values of <0.05 were considered significant. Survival experiments were analyzes using log-rank Mantel- Cox test for analysis with all groups using numbers of mice indicated. Bar graphs were compared utilizing two-tailed unpaired t test. Error bars are the SEM from independent samples of each represented experiment.

Example 2

Treatment with Live Attenuated *T. gondii* Increases Survival in Mice with Intraperitoneally Disseminated Pancreatic Cancer Tumor To examine the efficacy of CPS and OMUP mutants in aggressive pancreatic cancer, mice were injected intraperitoneally (i.p.) with Pan02 cells to simulate late-stage metastatic disease progression (Wennier, et al. (2012) Mol. Ther. 20:759-768). Mice were treated with CPS, OMUP or given control PBS and survival was tracked. Treatment with CPS (FIG. 1A) or OMUP (FIG. 1B) resulted in increased survival of mice exposed to pancreatic cancer. To further analyze treatment, the doses of CPS and OMUP mutants administered were increased. While there was a delay in the onset of metastatic disease, long term, there was still a 15-20% long-term survival rate between slow dose and rapid dose treatments (FIGS. 1A and 1B).

Figure 2:
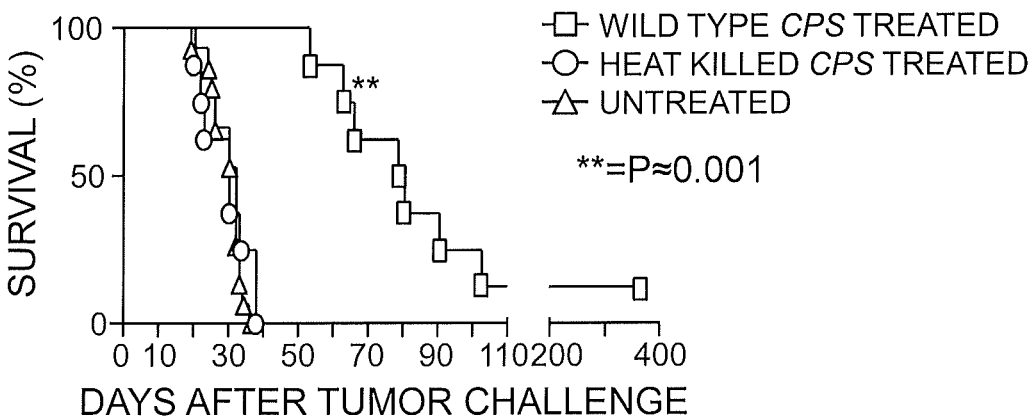
FIG. 2 shows that efficacy of CPS mutant treatment relies on active invasion of live CPS mutant into host cells in the tumor environment. Pan02 ($1\times10^6$) cells were injected into each mouse (n=8). Mice were treated with heat-killed CPS mutant or live CPS mutant on days 7, 8, 11, 12, 24 and 36 post-tumor inoculation. Survival was monitored for more than 300 days.
Figure 3A:
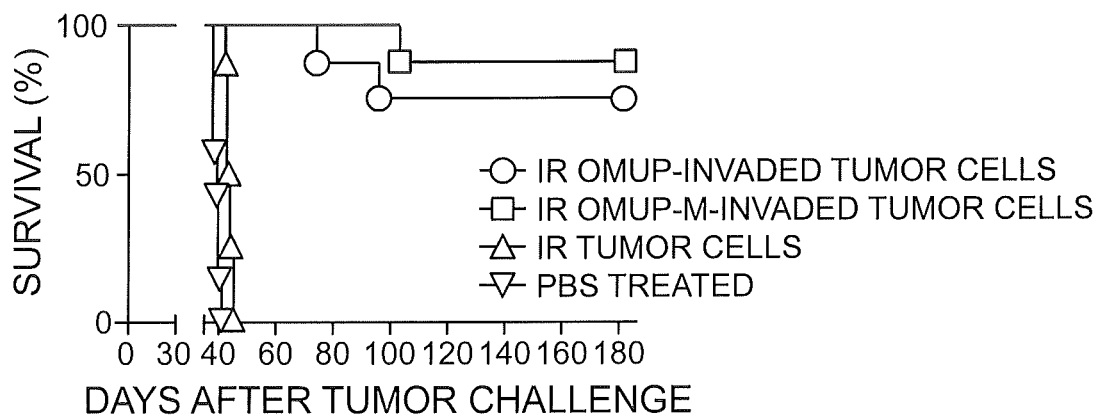
FIGS. 3A-3B show that a uracil auxotroph, mesothelin expressing vaccine protects mice from ovarian cancer and stimulates life-long immunity to ovarian cancer. Mice (n=8) were vaccinated with irradiated ovarian ID8-Defb29/Vegf-A tumor cells (IR tumor cells), with irradiated OMUP-invaded ovarian ID8-Defb29/Vegf-A tumor cells (IR OMUP-invaded tumor cells), or with irradiated OMUP-mesothelin expressing-invaded ovarian ID8-Defb29/Vegf-A tumor cells (IR OMUP-M-invaded tumor cells) on days 0 and 14. On day 21 all groups of mice were challenged with aggressive ovarian ID8-Defb29/Vegf-A tumors and survival was monitored (FIG. 3A). Age-matched control mice or mice that survived the tumor challenge (from FIG. 3A) for 6 months were re-challenged with ovarian ID8-Defb29/Vegf-A tumors and survival was monitored for 200 days (FIG. 3B).

It has been demonstrated that *T. gondii* unable to actively invade does not elicit the same responses as live *T. gondii* (Goldszmid, et al. (2009) *J. Exp. Med.* 206: 399-410). Given that live CPS mutant appeared to elicit responses beneficial to tumor survival, it was determined whether or not heat-killed CPS mutant conferred the same survival advantage. Heat-killed CPS mutant was administered using the rapid interval treatment and compared with survival of live CPS mutant-treated and untreated mice. Treatment including the use of heat-killed CPS mutant failed to provide a survival advantage to mice (FIG. 2).

Example 3

*T. gondii* Mutant Treatment Increases Myeloid Cells and Triggers Activation of these Populations To examine alterations in the cellular composition of the tumor microenvironment, Pan02 tumors were established and subsequently treated 14 days post-tumor inoculation with OMUP. The composition of the local microenvironment was then analyzed on days 1, 2, 4, 7 and 10 post-treatment. Following OMUP treatment, local B cells were reduced within 18 hours and continued to decline up to 10 days post-treatment. This population of cells has been implicated in promoting tumor progression by secreting pro-tumorigenic cytokines involved in skewing Th1 and Th2 immunity (Joyce & Pollard (2009) *Nat. Rev. Cancer* 9:239-252; Gabrilovich, et al. (2012) *Nat. Rev. Immunol.* 12:253-268).

Treatment with OMUP also increased the population of dendritic cells and this population increased up to 4 days post-treatment with numbers fully declined by day 10. Interestingly, macrophage populations sharply decreased following exposure to OMUP treatment when compared to untreated mice. A decrease in the tumor-associated macrophages following treatment was of interest as it is the suppressive capabilities of this population that plays a large role in maintaining the immunosuppression of the tumor microenvironment through development of disease (Clark, et al. (2007) *Cancer Res.* 67:9518-9527). Given the ability of *T. gondii* to preferentially invade and activate myeloid cells, it was determined how the activation of this cell population is altered following treatment with *T. gondii*. This analysis was carried out using CFSE-labeled OMUP to track invaded populations and determine how these cells differ in activation from non-invaded and untreated cells (Gubbels, et al. (2005) *Infect. Immunol.* 73:703-711; Jensen, et al. (2011) *Cell Host Microbe* 9:472-483). Within 18 hours post-treatment, 32% of macrophages and 13% of dendritic within the peritoneum were invaded by CFSE-labeled OMUP. Following *T. gondii* infection, the co-stimulatory molecules CD80 and CD86 were upregulated by dendritic cells, which leads to engagement and activation of recruited T cells (Subauste, et al. (1998) *J. Immunol.* 160:1831-1840; Pepper, et al. (2008) *Immunol.* 180:6229-6236). To assess the ability of OMUP treatment to phenotypically activate invaded dendritic cell and macrophage populations, the surface expression of CD80 and CD86 was measured between untreated, invaded, and non-invaded myeloid cells from the peritoneal cavity of mice with established pancreatic cancer. Eighteen hours post-treatment, invaded dendritic cell populations largely upregulated CD80 and CD86 when compared to non-invaded cells within the treated tumor microenvironment and within the untreated tumor microenvironment. Similarly, invaded macrophages expressed high amounts of CD80 and CD86 with treated non-invaded populations expressing slightly significantly more CD86 that the untreated counterparts within the tumor microenvironment. These data highlight the ability of OMUP treatment to recruit host responsive cells to the tumor microenvironment as well as begin local reversal of suppression by invading tumor-associated populations and reprogramming them in order to initiate downstream responses.

Example 4

*T. gondii* Mutant Treatment Stimulates IL-12 Production by Myeloid Cells and Depends on its Production Production of IL-12 is critical to the host immune response to *T. gondii* and the OMUP strain induces large amounts of this cytokine following invasion (Gigley, et al. (2009) *J. Immunol.* 182:1069-1078). Therefore, the levels of IL-12 produced following CPS and OMUP mutant injection were examined in Pan02 tumor-bearing mice. Following a single dose treatment, IL-12p40 and IL-12p70 production was measured on days 1, 2, 4, 6 and 7 post-treatment in the local tumor microenvironment and in the blood. Tumor bearing mice exhibited a significant increase in IL-12p40 production within 24 hours after treatment. Within 48 hours, a significant amount of IL-12p70 was detected locally with a sustained presence 4 days post-treatment. Interestingly, there was production of IL-12p70 by untreated mice on day 4; however, this cytokine production diminished as quickly as it appeared and did not benefit the untreated tumor-bearing mice.

Given the recruitment and activation of macrophages and dendritic cells to the local microenvironment, the production of IL-12p40 by these populations was examined. One day after treatment, the total number of IL-12p40 producing dendritic cells in the treated tumor bearing mice was significantly higher than in the untreated tumor bearing mice. This population increased two days after treatment with the IL-12p40 producing macrophages in untreated animals remaining significantly lower. Macrophage populations within treated mice also increased their production of IL-12p40 significantly over untreated mice. In addition to these sustained local IL-12 responses, the levels of systemic IL12p70 remained significantly higher in treated compared untreated mice. These data highlight the potential of an attenuated mutant of *T. gondii* to begin stimulating local antitumor responses soon after treatment and drive systemic responses that could lead to increased recruitment of immunostimulatory cells to the local microenvironment.

Since IL-12 is potently induced following treatment, it was posited that production of IL-12 is critical to the efficacy of treatment. IL-12p35$^{-/-}$ were treated with CPS, OMUP or PBS and compared with wild-type CPS or OMUP treated and wild-type untreated mice for the ability to survive Pan02 tumors. Treated IL-12p35$^{-/-}$ mice were unable to be protected against Pan02 tumors and succumbed to disease at the same rate as untreated IL-12p35$^{-/-}$ and wild-type untreated mice. Previous studies have shown that the majority of IL-12 production relies on the TLR adapter molecule MyD88 (Denkers, et al. (2012) *Infect. Immun.* 80:476-482). To determine whether this observation held true for CPS or OMUP therapeutic benefit, MyD88$^{-/-}$ mice were injected peritoneally with Pan02 cells and then treated with CPS or OMUP or with PBS as a vehicle. MyD88$^{-/-}$ CPS or MyD88$^{-/-}$ OMUP treated mice were nonresponsive to therapy and succumbed to disease at the same rate as untreated mice. These data demonstrate the importance of IL-12 signaling and production in maintaining the efficacy of treatment in the immunosuppressive pancreatic tumor microenvironment.

Example 5

*T. gondii* Mutant Treatment Increases Local Accumulation of Activated T Cells within the Tumor Microenvironment Infiltration of the tumor microenvironment by T cells is a good prognostic marker for antitumor responses in the premalignant phase of cancer (Boon, et al. (2006) *Annu. Rev. Immunol.* 24:175-208; Rosenberg (2001) *Nature* 411:380-384). Unfortunately, over time, these antitumor cells are subjected to immunosuppression by tumor and the recruitment of immunosuppressive cells such as myeloid-derived suppressor cells and regulatory T cells (Motz & Coukos (2013) *Immunity* 39:61-73). OMUP increases both CD4 and CD8 T cells locally in the context of ovarian cancer and melanoma. In addition, OMUP has been shown to recruit tumor-specific T cells to the microenvironment in order to mediate tumor cell killing (Gigley, et al. (2009) *Infect. Immun.* 77:5380-5388; Gigley, et al. (2009) *J. Immunol.* 182:1069-1078; Baird, et al. (2013) *J. Immunol.* 190:469-478). With the recruitment of myeloid cells and the increase in IL-12 production by these cells locally and systemically in the tumor-bearing mice, it was posited that these early priming events driven by *T. gondii* mutant treatment lead to an increase in CD4 and CD8 T cells locally. By seven days post-treatment, local CD4 T cells were significantly higher in treated mice than untreated mice. In addition to increases in local CD4 T cells, CD8 T cells increased by day 4 and continued to accumulate out to day 10 post-OMUP treatment.

To determine whether local CD4 and CD8 T cells become activated following treatment of established pancreatic cancer with OMUP, CD4 and CD8 T cells 7 days post-OMUP treatment were examined for expression of CD62L, CD44, and CD69. Local CD4 T cells displayed a down-regulation of CD62L when compared to untreated animals with −26.6% of untreated CD4$^+$ T cells being CD62L$^{hi}$ when compared to −2.5% of treated CD4$^+$ T cells being CD62L$^{hi}$. Further examination of CD62L$^{lo}$ CD4$^+$ T cells from treated and untreated Pan02 tumor-bearing mice revealed that these cells also increased expression of CD44 and CD69 (common markers for an activated T cell). Similar to CD4 T cells, local CD8 T cells exhibited lower expression of CD62L and increased expression of CD44 and CD69. These data highlight the ability of OMUP to promote an antitumor environment by recruiting and activating naïve T cells, which phenotypically display the capability of fighting against tumor.

Example 6

Treatment with *T. gondii* Mutants Depends on Active Production of IFN-γ

The cytokine interferon-gamma (IFN-γ) has been known to play a large role in the generation of anti-tumor responses (Zaidi & Merlino (2011) *Clin. Cancer Res.* 17:6118-24; Dunn, et al. (2006) *Nat. Rev. Immunol.* 6:836-848). CPS is a potent inducer of this cytokine locally following i.p. injection (Gigley, et al. (2009) *J. Immunol.* 182:1069-1078). Given the capability of a *T. gondii* mutant to induce production of IFN-γ, the presence of IFN-γ in the tumor microenvironment of OMUP-treated tumor-bearing mice at day 1, 2, 4, 6 and 7 was compared to the presence of IFN-γ in untreated tumor-bearing mice. Starting around day 2 post-treatment, OMUP induced an increase in local IFN-γ production that peaked at day 6. Although the amount of IFN-γ decreased at day 7, its production remained significantly higher than in untreated animals. T cells are a frequent biological source of IFN-γ and given the increase in local T cells following treatment, it was posited that these newly recruited T cells would produce large amounts of IFN-γ in response to tumor. Seven days post-treatment, cells of the peritoneal lavage of OMUP-treated and untreated animals were isolated and an intracellular stain on CD4 and CD8 T cell populations was performed to assess the production of IFN-γ. The numbers of IFN-γ$^+$ CD4 and CD8 T cells significantly increased 7 days post-treatment while the numbers in untreated animals remained low. Systemic production of IFN-γ did not significantly change in comparison to untreated animals, speaking to a strong induction of local responses.

Given the local induction of IFN-γ following recruitment of T cells to the local tumor microenvironment and the crucial role IFN-γ plays in wild-type *T. gondii* infection, the role of CPS or OMUP mutant treatment in the antitumor response was analyzed. To address this, IFN-γ$^{-/-}$ mice were inoculated with Pan02 tumor and CPS or OMUP-treated and untreated animals were compared. Similar to the IL12p35$^{-/-}$ mice, loss in the ability to produce IFN-γ resulted in a loss of the therapeutic benefit of CPS and OMUP mutants. Thus, the active production of IFN-γ by infiltrating CD4 and CD8 T cells following *T. gondii* mutant treatment plays a role in the generation of antitumor responses.

Example 7

Efficacy of *T. gondii* Mutant Treatment Depends on CD8 T Cells

Both CD4 and CD8 T cells increase, display phenotypic activation, and produce local IFN-γ in response to OMUP treatment in Pan02 tumor-bearing mice. It has been shown that expansion of tumor infiltrating CD4 and CD8 T cells has a positive prognostic value in a clinical setting (Fukunaga, et al. (2004) *Pancreas* 28:e26-31; Wahab & Metzgar (1991) *Pancreas* 6:307-317). It has also been demonstrated that OMUP induces strong CD8 T cell responses in mice and these responses are important in the protective response to *T. gondii* (Jordan, et al. (2009) *Infect. Immun.* 77:3894-3901). In addition, CD4+ T cells appear to be less critical to CPS treatment and survival of a lethal *T. gondii* challenge (Gigley, et al. (2009) *J. Immunol.* 182:1069-1078). Natural killer (NK) cells are also known to be important in antitumor responses as this population also secretes IFN-γ when matured and activated (Zamai, et al. (2007) *J. Immunol.* 178: 4011-4016). Therefore, it was determined whether NK cells, CD4+ and/or CD8+ T cells contributed to the success of CPS and OMUP mutants as a treatment. Mice were injected i.p. with Pan02 cells and NK cells, CD4+ T cells or CD8+ T cells were depleted prior to and following treatment. Animals were then tracked for survival in the absence of these cell populations. The loss of CD4+ T or NK cells did nothing to ablate the therapeutic benefit following CPS or OMUP treatment. In contrast, loss of CD8+ T cells led to complete loss of therapeutic efficacy with CD8 depleted animals succumbing to disease at the same rate as untreated animals. In addition, mice genetically deficient in CD8 T cell function (CD8a$^{-/-}$ mice) also receive no therapeutic treatment benefit. These data highlight a critical role for *T. gondii* mutant-mediated recruitment of CD8 T cells to the local tumor microenvironment of mice.

To understand how these CD8 T cells could be functioning to promote anti-tumor responses, their capacity to produce IFN-γ in response to re-stimulation by pancreatic cancer cells was analyzed. Pan02 tumors were established for 14 days and a single dose of OMUP was administered. Ten days later, CD8+ T cells were isolated from the spleens of treated and untreated mice. These CD8+ T cells were re-exposed to irradiated Pan02 cells for 48 hours and IFN-γ spots were measured. Following re-exposure, CD8 T cells from OMUP treated mice produced twice the amount of IFN-γ in response to Pan02 antigen when compared to untreated mice. To determine if this response was driven by antigen specificity, the above experiment was repeated with ID8 and HFF cells as irradiated targets. The ID8 cell line was a murine-derived ovarian cancer cell line which would share epithelial-based antigens (such as mesothelin) in common with the Pan02 line while the HFF cells serve as an irrelevant antigen control for non-specific IFN-γ production. Although CD8 T cells from Pan02 tumor-bearing mice were able to recognize ID8 and HFF cells and produce significantly more IFN-γ in response to re-stimulation, the response to Pan02 cells remained over 2-fold higher than treated response to ID8 and 3-fold higher than response to HFF cells. This difference indicated a potential for antigen-specific responses following exposure to OMUP and its use in generating downstream memory responses to established pancreatic tumor.

Example 8

Efficacy of OMUP Treatment as Adjuvant in an Irradiated Tumor Cell Formulation

Figure 3B:
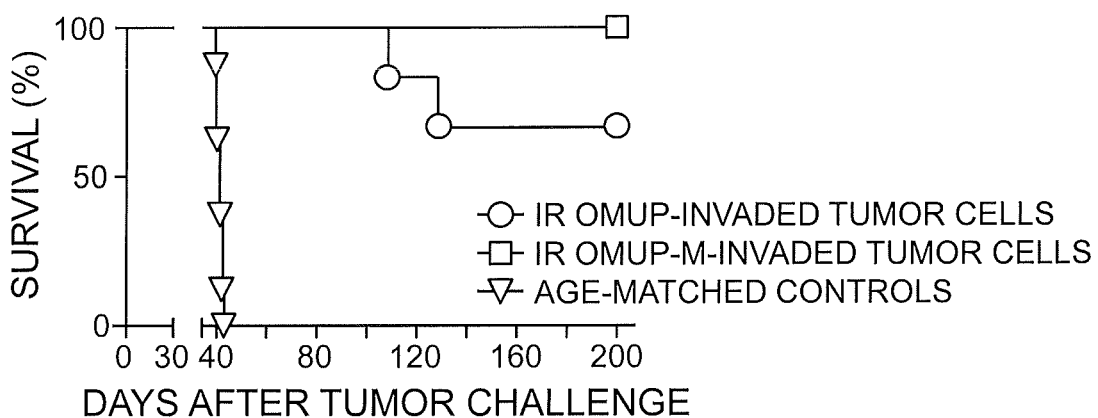

Irradiated whole cell tumor vaccines are of interest as whole cells provide a greater natural repertoire of tumor antigen epitopes that can stimulate a more robust immune response to tumors. However, adjuvants that can boost vaccine effectiveness of irradiated whole tumor cells formulations are limited. It has now been found that a *T. gondii* uracil auxotroph itself or in a vaccine formulation is an incredibly potent adjuvant for stimulating vaccine-induced immunity to tumor. In particular, *T. gondii* uracil auxotroph OMUP, a mesothelin expressing vaccine strain of OMUP, or tumor cells only were assessed for antitumor activity. Tumor cells were invaded in vitro with OMUP or with an OMUP strain exogenously expressing mesothelin (OMUP-M). The OMUP-M strain secretes the engineered mesothelin protein with a known mesothelin CD8 T cell epitope that is H-2kb-restricted (C57BL/6 mice). Tumor cells were invaded for 3 hours in vitro at an m.o.i. of 2, >85% parasite invasion of tumor cells was verified, and all non-invaded parasites were then removed by washing. Tumor cells or invaded tumor cells were collected by trypsinization and cells were irradiated at 15 krad prior to vaccination of mice (2 million cell vaccine dose). The irradiated tumor cells were poorly immunogenic and mice survived just 2 or 3 days longer than PBS vaccinated mice. By contrast, all mice that received the OMUP vaccine demonstrated strong protection against primary tumor challenge (FIG. 3A), and in surviving mice, against tumor re-challenge 6 months later (FIG. 3B). The mesothelin expressing OMUP vaccine demonstrated superior protection in the primary challenge as well as in the re-challenge (100% long-term immunity to tumor). Given that pancreatic tumors also express mesothelin, a *T. gondii* uracil auxotroph expressing mesothelin is also of use in the prevention of pancreatic cancer.

Figure 4:
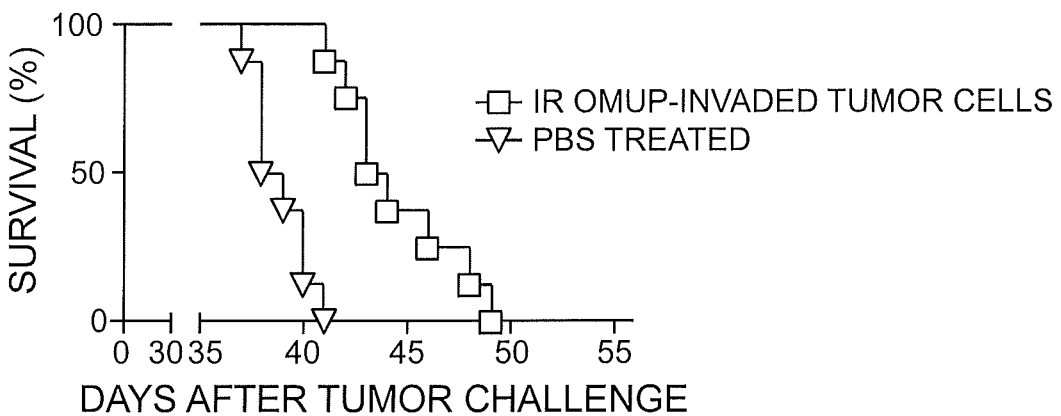
FIG. 4 shows the therapeutic efficacy of uracil auxotroph vaccines administered with irradiated tumor cells in tumor treatment. Mice (n=8) bearing 8-day old aggressive ovarian ID8-Defb29/Vegf-A tumors were treated with irradiated OMUP-invaded ovarian ID8-Defb29/Vegf-A tumor cell vaccine and survival was monitored.

In addition to prevention, the irradiated tumor cell-*Toxoplasma* uracil auxotroph vaccine was also capable of therapeutic efficacy against pre-existing tumors. Mice (n=8) bearing 8-day old aggressive ovarian ID8-Defb29/Vegf-A tumors were treated with the irradiated OMUP-invaded tumor cell vaccine and survival was monitored. A single treatment of established tumors provided equivalent efficacy as compared to tumor treatment with cps or OMUP alone (FIG. 4). Thus, these data show that the irradiated whole cell vaccines are also capable of therapeutic efficacy on pre-existing tumors, as well as having the ability to potently stimulate immunity to tumors.

What is claimed is:

1. A method for treating pancreatic cancer comprising administering at least six doses of an irradiated pancreatic tumor cell to a subject in need of treatment over a period of 36 days, wherein the irradiated tumor cell harbors an effective amount of an attenuated mutant of *Toxoplasma gondii* comprising a knockout mutation of orotidine 5'-monophosphate decarboxylase; a knockout mutation of uridine phosphorylase; and nucleic acids encoding one or more of annexin A2, plectin-1, fetoacinar pancreatic protein, or tubulin tyrosine ligase-like family member 4, thereby treating the subject's pancreatic cancer.

2. The method of claim 1, wherein the attenuated mutant further comprises in its genome nucleic acid molecules encoding one or more exogenous proteins.

* * * * *